United States Patent [19]
Camino et al.

[11] Patent Number: 6,086,613
[45] Date of Patent: Jul. 11, 2000

[54] SPACER ASSEMBLY FOR USE IN SPINAL SURGERIES

[75] Inventors: Thomas S. Camino, Eldersburg, Md.; John D. Malone, Beachwood, Ohio

[73] Assignee: DePuy Acromed, Inc., Cleveland, Ohio

[21] Appl. No.: 09/218,745

[22] Filed: Dec. 22, 1998

Related U.S. Application Data

[60] Provisional application No. 60/068,660, Dec. 23, 1997.
[51] Int. Cl.[7] .................................. A61F 2/30; A61F 2/44
[52] U.S. Cl. ................................................ 623/17; 623/16
[58] Field of Search .......................... 623/17, 16; 606/66, 606/61

[56] References Cited

U.S. PATENT DOCUMENTS

| | | |
|---|---|---|
| 2,677,369 | 5/1954 | Knowles . |
| 4,309,777 | 1/1982 | Patil . |
| 4,820,305 | 4/1989 | Harms et al. . |
| 4,834,757 | 5/1989 | Brantigan . |
| 4,878,915 | 11/1989 | Brantigan . |

(List continued on next page.)

FOREIGN PATENT DOCUMENTS

| | | |
|---|---|---|
| 0 268 115 A1 | 5/1988 | European Pat. Off. . |
| 0 666 068 A1 | 8/1995 | European Pat. Off. . |
| 0 727 196 A1 | 8/1996 | European Pat. Off. . |
| 0 732 093 A2 | 9/1996 | European Pat. Off. . |
| 2 733 413 | 10/1996 | France . |
| 40 12 622 C1 | 7/1991 | Germany . |
| 44 23 257 A1 | 1/1996 | Germany . |
| 195 09 317 A1 | 9/1996 | Germany . |
| 196 22 827 A1 | 12/1997 | Germany . |

OTHER PUBLICATIONS

G.L. Lowery and J. Harms: "Titanium Surgical Mesh for Vertebral Defect Replacement and Intervertebral Spacers", Manual of Internal Fixation of the Spine (1996), Lippincol-1–Raven Publishers, Philadelphia XP002102821, pp. 127–146.

"Bench Test Report DM–004 Titanium Surgical Mesh, Evaluation of Titanium Surgical Mesh in High Cycle Fatigue Loading Scenarios," #5M496, 0604–51–000, ©1996 DePuy Motech, Inc. (3 pages).

J. Harms and D. Stoltze, "The Indications and Principles of Correction of Post–Traumatic Deformities," Eur. Spine J. (1992) 1:142–151.

J. Harms, M.D., "Screw–Threaded Rod System in Spinal Fusion Surgery," Spine: State of the Art Reviews—vol. 6, No. 3, Sep. 1992, pp. 541–575.

"Bench Test Report DM–003 Titanium Surgical Mesh, Evaluation of Titanium Surgical Mesh in Multiple Static Compressive Loading Scenarios," #5M496, 0604–50–000, ©1996 DePuy Motech, Inc. (3 pages).

Gary L. Lowery and Jürgen Harms, "Titanium Surgical Mesh for Vertebral Defect Replacement and Intervertebral Spacers," Manual of Internal Fixation of The Spine, edited by John S. Thalgott and Max Aebi, Lippincott–Raven Publishers, Philadelphia, ©1996, pp. 127–146.

"The DePuy Motech Surgical Titanium Mesh, The Right Size, The Right Shape, Right Now," 10M595 0604–29–000 (Rev. 1), ©1994 DePuy Motech Inc. (1 page).

"Surgical Titanium Mesh Product Catalogue,"#9067–14 DePuy Motech Inc. (10 pages).

"Moss® Modular Segmental Spinal Instrumentation Product Catalogue," #9067–15 DePuy Motech Inc. (6 pages).

*Primary Examiner*—Paul J. Hirsch
*Assistant Examiner*—Michael B. Priddy

[57] ABSTRACT

A spacer assembly is provided for use in spinal surgeries. The spacer assembly includes a spacer having opposite ends and a side wall extending between the opposite ends and at least one end cap coupled to at least one of the opposite ends of the spacer. Each end cap includes an inner end facing the spacer, an outer end, and a side wall extending between the inner and outer ends. The side wall of each end cap is formed for engagement with the side wall of the spacer to provide a mechanical connection between the end cap and the spacer.

33 Claims, 10 Drawing Sheets

U.S. PATENT DOCUMENTS

| | | |
|---|---|---|
| 4,997,432 | 3/1991 | Keller . |
| 5,026,373 | 6/1991 | Ray et al. ................................. 606/61 |
| 5,147,402 | 9/1992 | Bohler et al. . |
| 5,192,327 | 3/1993 | Brantigan . |
| 5,306,307 | 4/1994 | Senter et al. . |
| 5,425,772 | 6/1995 | Brantigan . |
| 5,458,638 | 10/1995 | Kuslich et al. . |
| 5,522,899 | 6/1996 | Michelson . |
| 5,554,191 | 9/1996 | Lahille et al. . |
| 5,571,190 | 11/1996 | Ulrich et al. . |
| 5,571,192 | 11/1996 | Schönhöffer . |
| 5,591,235 | 1/1997 | Kuslich . |
| 5,593,409 | 1/1997 | Michelson . |
| 5,607,424 | 3/1997 | Tropiano . |
| 5,609,635 | 3/1997 | Michelson . |
| 5,609,636 | 3/1997 | Kohrs et al. . |
| 5,609,637 | 3/1997 | Biedermann et al. ..................... 623/17 |
| 5,658,337 | 8/1997 | Kohrs et al. .............................. 623/17 |
| 5,669,909 | 9/1997 | Zdeblick et al. . |
| 5,702,449 | 12/1997 | McKay ...................................... 623/17 |
| 5,702,451 | 12/1997 | Biedermann et al. ..................... 623/17 |
| 5,702,455 | 12/1997 | Saggar ...................................... 623/17 |
| 5,713,899 | 2/1998 | Marnay et al. . |
| 5,716,415 | 2/1998 | Steffee . |
| 5,749,916 | 5/1998 | Richelsoph ............................... 623/17 |
| 5,766,253 | 6/1998 | Brosnahan, III ......................... 623/17 |
| 5,785,710 | 7/1998 | Michelson ................................ 606/61 |
| 5,865,845 | 2/1999 | Thalgott ................................... 623/17 |
| 5,885,299 | 3/1999 | Winslow et al. ......................... 606/99 |
| 5,972,031 | 10/1999 | Biedermann et al. ..................... 623/17 |

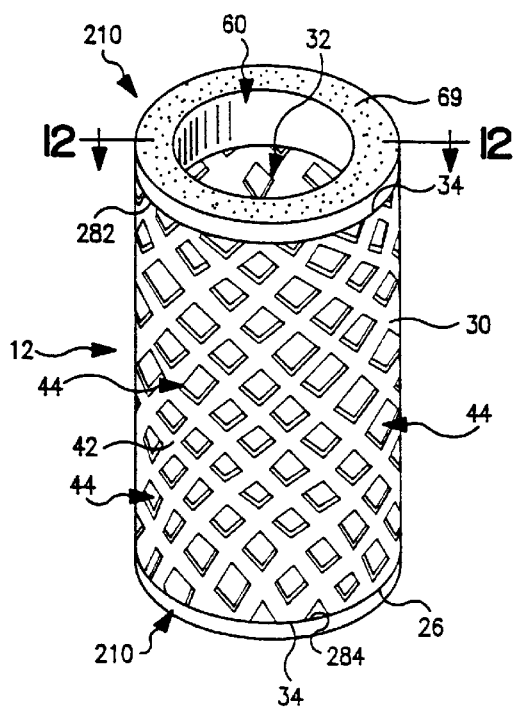
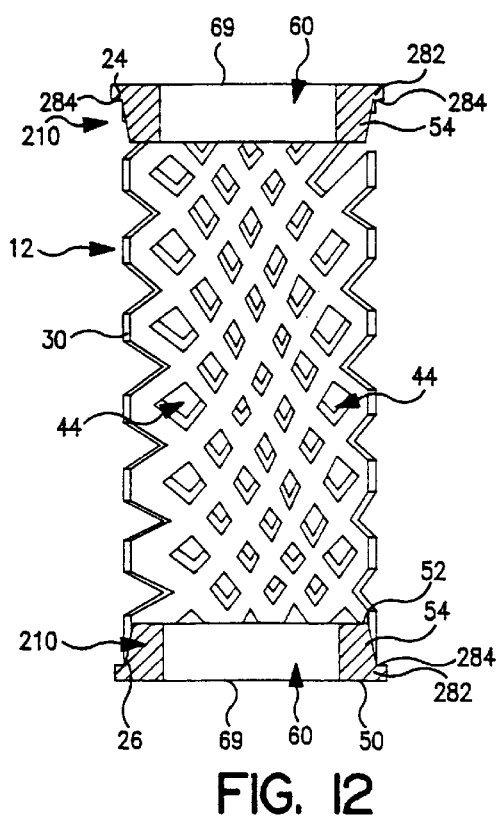
FIG. 11
FIG. 12

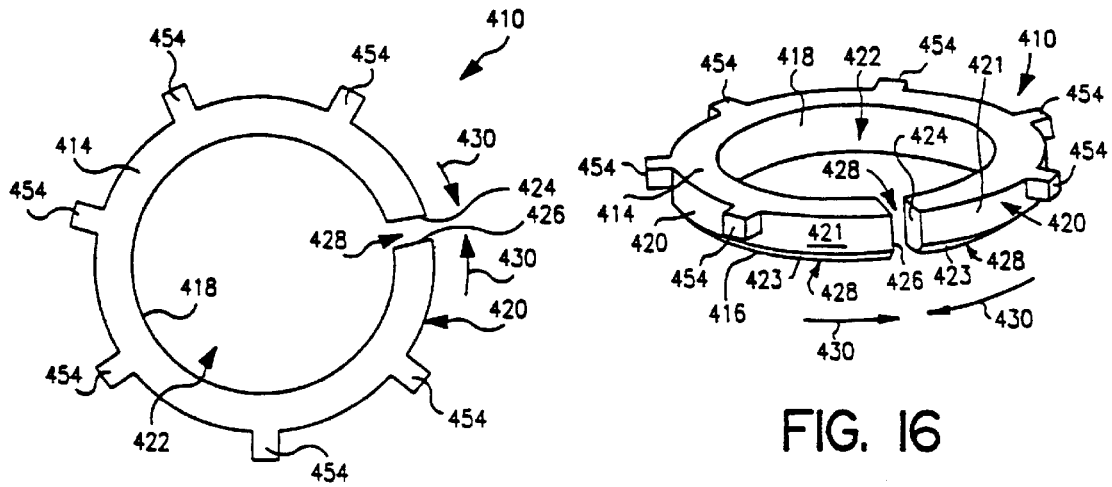
FIG. 15
FIG. 16
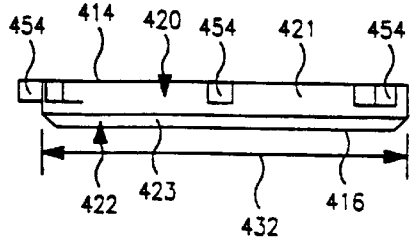
FIG. 17
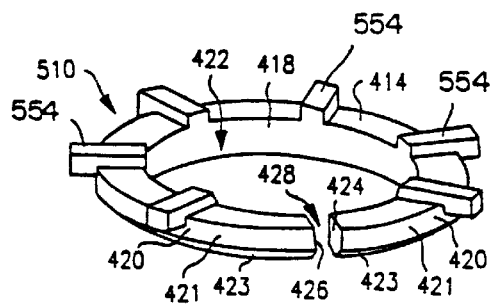
FIG. 18

SPACER ASSEMBLY FOR USE IN SPINAL SURGERIES

This claims priority under 35 U.S.C. §119(e) of Serial No. 60/068,660 filed Dec. 23, 1997.

BACKGROUND AND SUMMARY OF THE INVENTION

The present application relates to spinal instrumentation systems, more particularly to spacer assemblies for use in interbody fusion procedures of the spine. Most particularly, the present invention relates to end caps for use with spacers that are used in spinal surgeries.

There has been a gradual acceptance of interbody fusion as a procedure for a number of spinal disorders. Interbody fusion procedures employ the use of surgical mesh tubes, see for example "Chapter 10: Titanium Surgical Mesh for Vertebral Defect Replacement and Intervertebral Spacers", Gary L. Lowery and Jürgen Harms, *Manual of Internal Fixation of the Spine,* edited by John S. Thalgott and Max Aebi, Lippincoll-Raven Publishers, Philadelphia, 1996, which is incorporated herein by reference. The surgical mesh tubes are used to reinforce weak, bony tissues in orthopaedic procedures and they act as a structural support for the spine. Moreover, a mesh pattern in the conventional surgical mesh tubes provides access for bone to grow and fuse within the tube. These surgical mesh tubes are often formed of titanium and are available in varying shapes and sizes. In addition, surgical mesh tubes can be trimmed on site by the surgeon to better provide an individual fit for each patient.

Internal rings, connector screws, and fenestrated end plates have been added to the surgical mesh tube. See, for example, "Titanium Surgical Mesh for Vertebral Defect Replacement and Intervertebral Spacers", Gary L. Lowery and Jürgen Harms, *Manual of Internal Fixation of the Spine,* edited by John S. Thalgott and Max Aebi, Lippincoll-Raven Publishers, Philadelphia, 1996. As discussed in the before mentioned article, conventional rings attach to the contoured mesh through the use of screws. The conventional rings strengthen the surgical mesh tube by acting as a reinforcement to aide in better distributing the axial loads previously taken wholly by the edge of the surgical mesh tube.

According to the present invention a spacer assembly is provided for use in spinal surgeries. The spacer assembly comprises a spacer having opposite ends and a side wall extending between the opposite ends and at least one end cap coupled to at least one of the opposite ends of the spacer. Each end cap includes an inner end facing the spacer, an outer end, and a side wall extending between the inner and outer ends. The side wall of the end cap is formed for engagement with the side wall of the spacer to couple the end cap and spacer together.

In preferred embodiments, the spacer includes a passageway between the opposite ends and the inner end of the end cap extends into the passageway. The side wall of the end cap converges from the outer end toward the inner end to wedge fit the end cap in the spacer. In addition, the end cap includes at least one projection coupled to the side wall and formed to engage the spacer. The projection blocks sliding movement of the end cap in the passageway of the spacer. Also, the outer end includes an outer surface that promotes bone ingrowth, such as for example a porous coating or a serrated surface. Preferably, the engagement of the end cap side wall and the projection with the side wall of the spacer 12 provides the sole mechanical connection between the end cap and the spacer.

Alternatively, the side wall of the end cap is formed to include a slot extending between the outer and inner ends. The slot allows the side wall of the end cap to be compressed as it is inserted into the passageway of the spacer. Once positioned in the passageway, the side wall expands toward the side wall of the spacer to friction lock the end cap in the passageway of the spacer. At least one projection extends from the side wall of the compressible end cap for engagement with the spacer to block sliding movement of the end cap in the passageway.

Still further, the side wall of the spacer includes an outer surface and an alternative end cap is formed to extend over the opposite end of spacer and be coupled to the outer surface. The end cap includes an outer end, an inner end, and a side wall that extends between the outer and inner ends. In addition, the side wall includes a slot extending between the outer and inner ends. The slot allows the side wall of the end cap to be expanded as it is placed about the end of the spacer. Once positioned about the outer surface of the spacer, the side wall of the end cap contracts toward the side wall of the spacer to friction lock the end cap on the side wall of the spacer. At least one projection extends from the side wall of the compressible end cap for engagement with the spacer to block sliding movement of the end cap in the passageway.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 11 is an isometric view of the spacer of FIG. 2 and end caps in accordance with an alternative embodiment of the present invention showing the end caps having a porous coated top surface and a lip extending about the circumference of the end cap to prevent the end cap from slipping down within a passageway of the surgical mesh tube;

FIG. 12 is a cross-sectional view taken along the lines 12—12 of FIG. 11 showing the tapered side wall of the end cap and the lip engaging peaks of the side wall to prevent the end caps from sliding in the passageway of the spacer;

FIG. 15 is a top view of an end cap in accordance with an alternative embodiment of the present invention showing the end cap including a side wall having a slot formed therein and teeth coupled to the side wall;

FIG. 16 is a perspective view of the end cap of FIG. 15 showing the slot extending between the outer and inner ends of the end cap to permit compression of the end cap;

FIG. 17 is a side view of the end cap of FIG. 15 showing the side wall including a first side wall portion and a tapered second side wall portion;

FIG. 18 is a perspective view of an end cap in accordance with an alternative embodiment of the present invention showing the end cap outer and inner ends, a side wall extending between the outer and inner ends, and teeth extending upwardly from the outer end and away from the side wall;

DETAILED DESCRIPTION OF THE DRAWINGS

Figure 1:
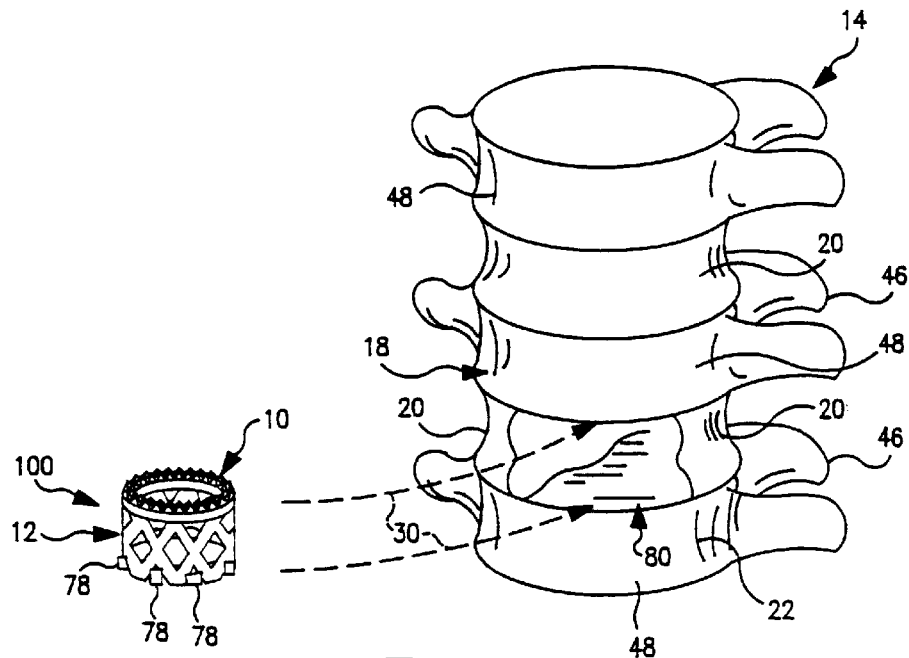
FIG. 1 is a perspective view of an anterior portion of a spine, a spacer assembly in accordance with the present invention, and showing a portion of one disc removed from the spine to form a disc space and the inter-vertebral spacer sized for extension into the disc space.

End caps 10 are provided in accordance with the present invention for use with vertebral body spacers 12 in a spine 14 during disc-replacement or vertebral body replacement surgery to form a spacer assembly 100. As shown in FIG. 1, end cap 10 is coupled to spacer 12 and is suitable for placement into an anterior portion 18 of spine 14. This placement may be done to replace an inter-vertebral disc 20 or to replace a vertebral body 22 or multiple versions of each.

Figure 2:
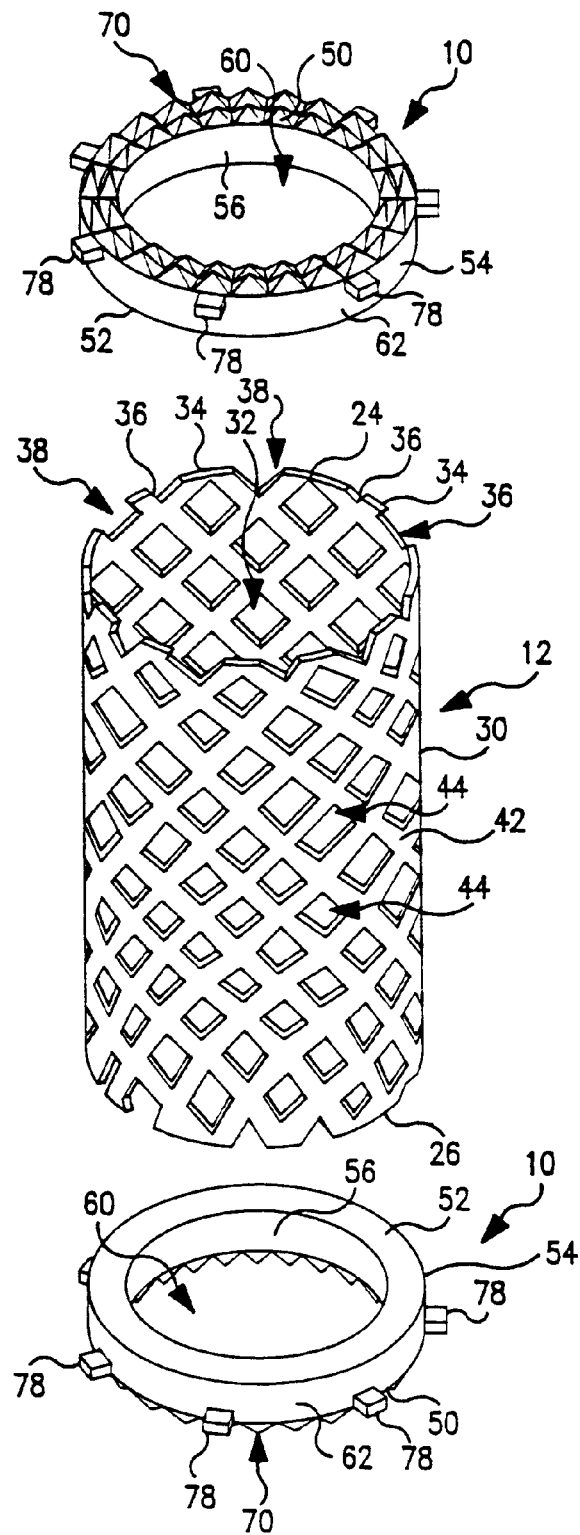
FIG. 2 is an exploded isometric view of the spacer assembly of FIG. 1 showing the spacer assembly including a spacer and two end caps of the present invention.

Spacer 12 is, for example, a surgical mesh tube constructed of titanium mesh. Spacer 12 houses bone (not shown) such that spacer 12 fuses to spine 14 to where there will be generally no movement between spacer 12 and spine 14 to reduce a patient's pain. Spacer 10 includes opposite ends 24, 26 and a cylindrical side wall 30 extending between ends 24, 26 and defining a passageway 32 having a predetermined inner diameter 28. Opposite ends 24, 26 each include peaks 34 and valleys 36 that form detents 38. In addition, side wall 30 has an inner surface 40, an outer surface 42, and apertures 44 extending between inner and outer surfaces 40, 42. As shown in FIG. 2, apertures 44 are generally diamond shaped and positioned to lie in a diamond-like pattern relative to one another. It is appreciated, however, that apertures 44 may have a variety of shapes and sizes and be positioned in a variety of patterns to promote bone ingrowth during the healing process. In addition to titanium mesh, end caps 10 are suitable for use with other forms of spacers that are also used in anterior portion 18 of spine 14. Specifically, end caps 10 are suitable for use with mesh spacers constructed in a variety of sizes and from a variety of metals, composites, tissue, or bone, or any other type of mesh spacer designed to be placed into spine 14 as a spinal spacer.

Referring now to FIG. 1, spine 14 includes anterior portion 18 and a posterior portion 46. In addition, spine 14 is constructed of vertebral bodies 48, seven of which are cervical vertebral bodies, twelve of which are thoracic vertebral bodies, and five of which are lumber vertebral bodies. End caps 10 of the present invention are coupled to spacer 12 that is delivered to anterior portion 18 or posterior portion 46 of spine 14 whether it is cervical, thoracic or lumber. Spacers 12 can be designed to replace either disc 20, as shown in FIG. 1, or vertebral body 48. Insertion of spacers 12 into spine is further described in U.S. Patent Application entitled "Insertion Instruments and Method for Delivering a Vertebral Body Spacer," to Urbahns et. al., filed on Dec. 18, 1998, which is incorporated herein by reference.

Figure 3:
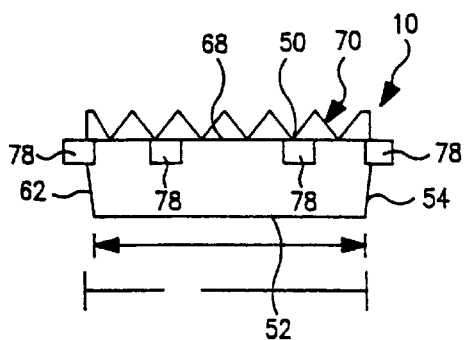
FIG. 3 is a side view of the end cap of FIG. 2 showing the end cap including an outer end, an inner surface, a tapered side wall extending between the outer and inner surfaces, teeth extending outwardly from the side wall, and the outer end including a serrated surface.
Figure 4:
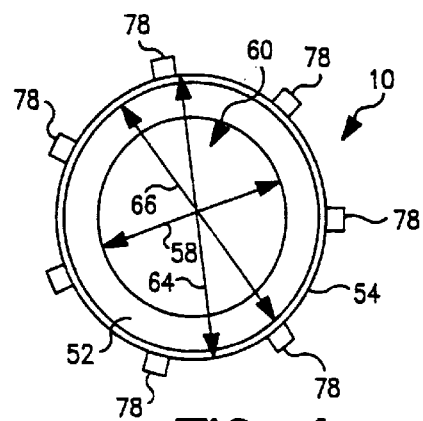
FIG. 4 is a bottom view of the end cap of FIG. 3 showing the side wall including an outer surface and an inner surface defining a passageway and the teeth extending from the outer surface in a spaced-apart relationship relative to one another.
Figure 5:
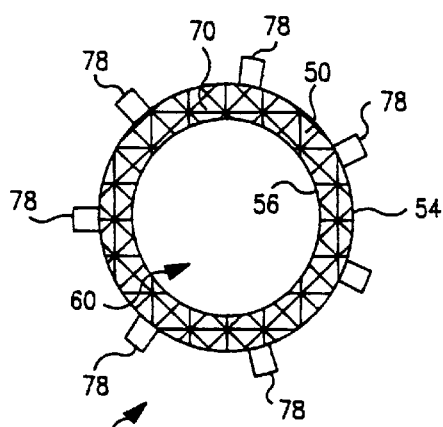
FIG. 5 is a top view of the end cap of FIG. 3 showing the serrated surface of the outer end.

As shown in FIG. 2, end cap 10 is coupled to either end 24, 26 of spacer 12 for use in interbody fusion surgeries. End cap 10, remains at either end 24, 26 of spacer 12 without slipping down within passageway 32. As shown in FIGS. 2–5, end cap 10 is formed to include an outer end 50, an inner end 52, and a tapered side wall 54 converging from outer end 50 toward inner end 52. Referring now to FIG. 4, side wall 54 includes a generally cylindrical inner surface 56 having a constant diameter 58 and defining a passageway 60 and an outer surface 62. While end cap 10 is shown in FIGS. 4 and 5 with generally circular outer and inner ends 50, 52, it is appreciated that outer and inner ends 50, 52 may be formed in a variety of shapes to cooperate with a variety of opposite ends 24, 26 of spacers 12 and may be positioned to lie generally parallel to one another or angled relative to one another. It is also appreciated that end caps 10 may vary in size to cooperate with a variety of spacers 12.

Outer surface 62 of side wall 54 cooperates with inner surface 40 of side wall 30 to form a friction lock between end cap 10 and spacer 12, eliminating the necessity of additional parts to couple end cap 10 and spacer 12 together. Referring now to FIG. 4, outer surface 62 has first outer diameter adjacent 64 to outer end 50 and a second outer diameter 66 adjacent to inner end 52. First outer diameter 64 is greater than second outer diameter 66 so that outer surface 62 of side wall 54 converges at about an 8 degree taper, as shown in FIG. 3. It is appreciated that side wall 54 may be formed at various angles so long as a friction lock is formed between end cap 10 and spacer 12 in accordance with the present disclosure. In addition, first outer diameter 64 of side wall 54 adjacent to outer end 50 of end cap 10 is generally equivalent to diameter 28 of spacer 14 so that outer end 50 is positioned to lie adjacent to end 24 of spacer 12.

Figure 6:
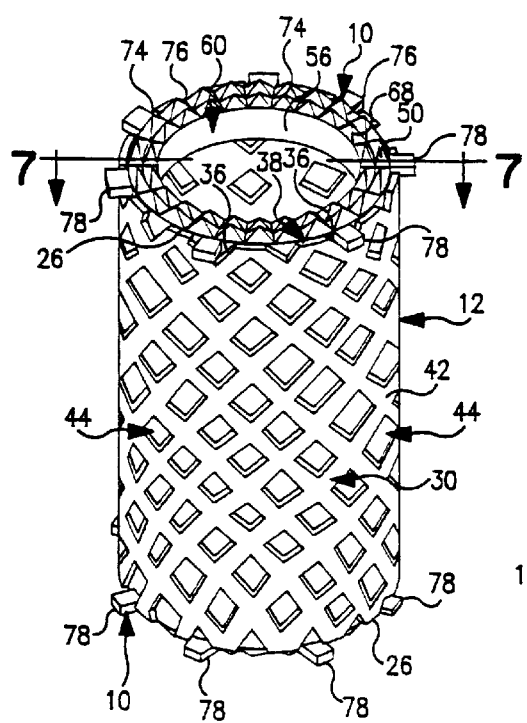
FIG. 6 is an isometric view of the spacer assembly of FIG. 2 following insertion of the end caps into the spacer showing the end caps having a serrated outer side and teeth spaced apart about the periphery of the end cap and engaging the spacer to hold the end cap in place.
Figure 7:
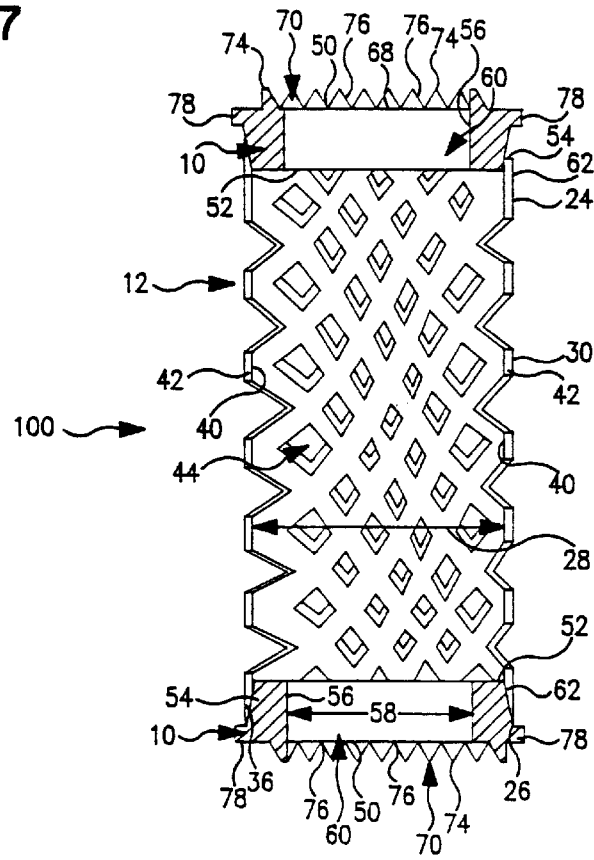
FIG. 7 is a cross-sectional view taken along the lines 7—7 of FIG. 6 showing the spacer including a cylindrical side wall defining a passageway and two end caps extending into the passageway and engaging the cylindrical side wall to wedge the end caps and spacer together.

As shown in FIG. 3, outer surface 62 is further formed to include projections or interdigitating teeth 78 that are spaced apart from another adjacent to outer end 50 of end cap 10. Referring now to FIGS. 6 and 7, teeth 78 are positioned on outer surface 62 such that when end cap 10 has been wedged within spacer 12, teeth 78 rest against valleys 36 of opposite ends 24, 26. Because each tooth 78 rests within detent 38, end cap 10 is thus prohibited from slipping within passageway 32 of spacer 12. The engagement of side wall 54 and teeth 78 with side wall 30 of spacer 12 provides the sole mechanical connection between end cap 10 and spacer 12. While end cap 10 is shown with seven teeth 78, it is appreciated that greater or fewer than seven teeth 78 may be coupled to outer surface 62 in accordance with the present disclosure.

Referring now to FIG. 6, outer end 50 of end cap 10 includes an outer side 68 formed to promote bone ingrowth. One type of outer side 68 that promotes bone ingrowth is for example, a porous coated finish 69, as shown in FIGS. 11 and 12. An alternative outer side 68 suitable for bone growth is a serrated outer surface 70. See FIGS. 1–7. Serrated surface 70 of end cap 10 includes peaks 74 and valleys 76. Peaks 74 and valleys 76 provide a rough surface and reduce movement against vertebral body 48. Although porous and serrated outer finishes 70 are described, it is appreciated that a variety of anti-skid surfaces that promote bone ingrowth may be used in accordance with the present disclosure.

When replacing disc 20 or vertebral bodies 48, the surgeon first removes damaged disc 20 or bodies 48 to create a space 80. See for example disc space 80 in FIG. 1. Once space 80 is formed, the surgeon selects the appropriate size of spacer 12 and at least one corresponding end cap 10. While only one end cap 10 and end 24 of spacer 12 will be discussed hereafter it is appreciated that the description and claims applies to greater than one end cap 10 and end 26. Referring now to FIG. 2, inner end 52 of end cap 10 is aligned with end 24 of spacer 12. Inner end 52 is inserted into passageway 32, as shown in FIG. 7, until outer surface 62 is wedged into engagement with side wall 30 of spacer to form a spacer assembly 100. At that time, teeth 78 will be positioned to lie within detents 38 preventing further migration of end cap 10 into passageway 32 of spacer 12. Once end cap 10 is coupled to spacer 12, spacer assembly 100 may be inserted into space 80 using a variety of surgical techniques. See, for example, U.S. Patent Application entitled "Insertion Instruments and Method for Delivering a Vertebral Body Spacer," to Urbahns et. al., filed on Dec. 18, 1998, which is incorporated herein by reference.

Figure 10:
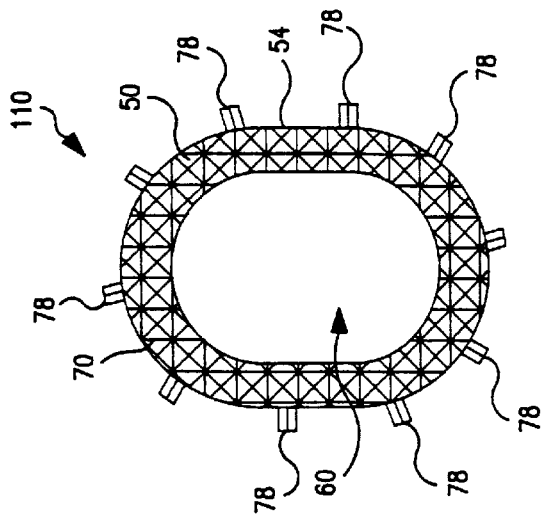
FIG. 10. is a top view of the end cap of FIG. 8 showing the serrated surface.
Figure 9:
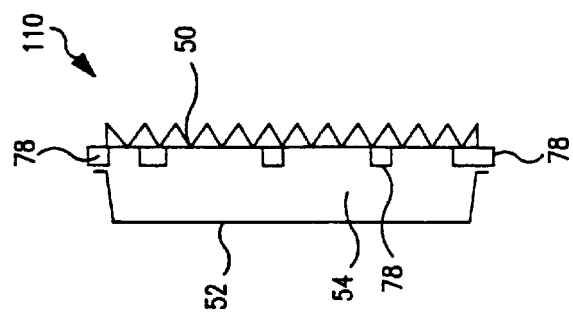
FIG. 9 is a side view of the end cap of FIG. 8 showing the end cap having an outer end with a serrated surface, and inner end, and a tapered side wall converging from the outer end toward the inner end.
Figure 8:
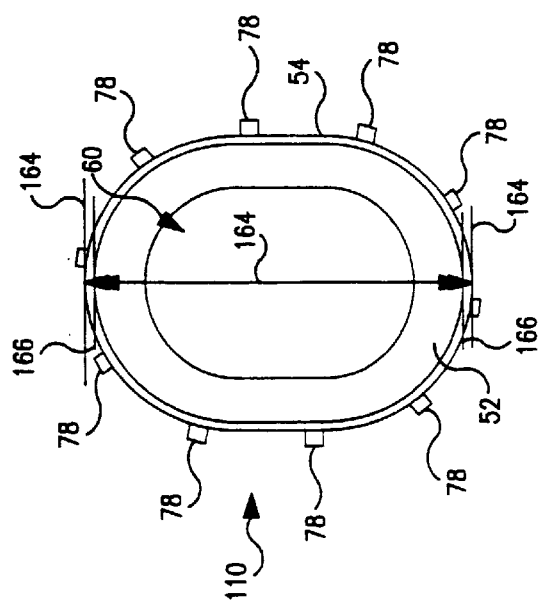
FIG. 8 is a bottom view of an end cap in accordance with an alternative embodiment of the present invention showing the end cap having an oval shape.

In an alternative embodiment of the present invention it is provided that an end cap 110 has an oval shape. See, FIGS. 8–10. End cap 110 is formed to cooperate with an oval-shaped spacer (not shown) that is formed identically to spacer 12, except for the oval shape of side wall 30. End cap 110 is formed similarly to end cap 10 and like reference numerals are use to denote like components. As shown in FIG. 8, end cap 110 has a first ring width 164 adjacent to outer end 50 and a second ring width 166 adjacent to inner end 152. First ring width 164 is greater than second ring width 166, so that outer surface 62 of side wall 54 converges from outer end 50 toward inner end 152 and forms about an 8 degree taper, as shown in FIG. 9. It is appreciated that the angle of taper may vary so long as end cap 110 may be wedged in spacer 12. Additionally, end cap includes ten teeth 78 coupled to outer surface 62. It is appreciated, however, that greater or fewer than ten teeth 78 may be coupled to outer surface 62.

In an alternative embodiment of the present invention, an end cap 210 is provided. End cap 210 is formed similarly to end cap 10 and like reference numerals are used to denote like components. As shown in FIGS. 11 and 12, end cap 210 includes a single projection or outer lip 282 extending from side wall 54 adjacent to outer end 50. Outer lip 282 extends about the circumference of outer end 50 and includes an inner face 284 that rests on peaks 34 of opposite ends 24, 26 respectively to prevent end cap 210 from slipping within passageway 32 of spacer 12. The engagement of side wall 54 and teeth lip 282 with side wall 30 of spacer 12 provides the sole mechanical connection between end cap 210 and spacer 12.

Figure 13:
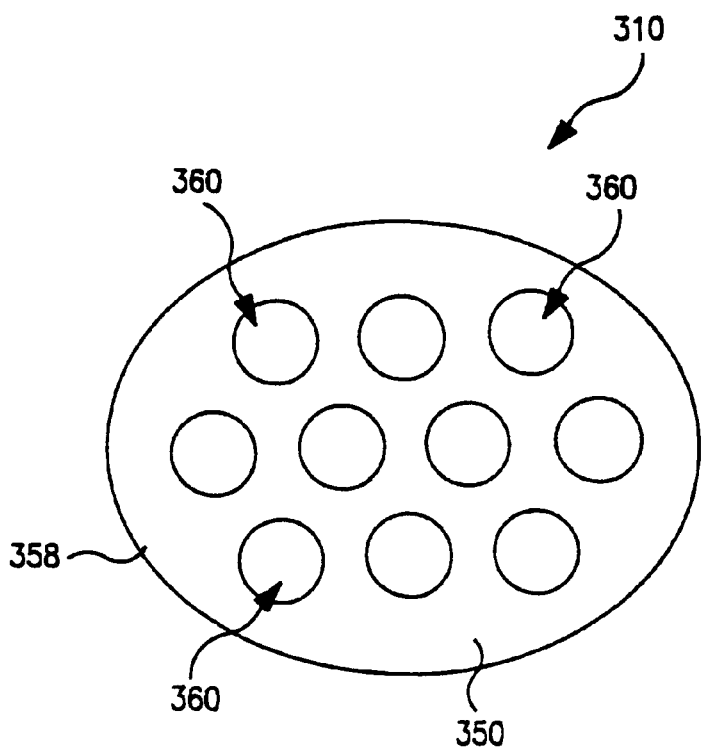
FIG. 13 is a top view of an end cap in accordance with an alternative embodiment of the present invention showing the end cap to include a solid plate formed with apertures therein.
Figure 14:
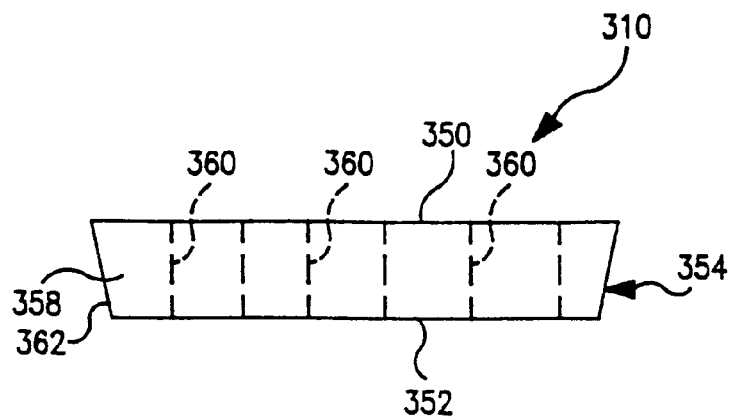
FIG. 14 is a side view of the end cap of FIG. 13 showing the apertures, in phantom, extending between the outer and inner ends of the end plate.

In still another embodiment of the present invention an end cap 310 is provided. As shown in FIGS. 13 and 14, end cap 310 is a solid plate 358 shown to have an oval shape and is suited particularly for use with osteoporotic bone. End cap 310 includes an outer end 350, an inner end 352, and a tapered side wall 354 converging from outer end 350 toward inner end 352. Referring now to FIG. 14, side wall 354 includes an outer surface 362. Outer surface 362 of side wall 354 is tapered similarly to outer surface 62 to form a friction lock with spacer 12. The engagement of side wall 354 with side wall 30 of spacer 12 provides the sole mechanical connection between end cap 310 and spacer 12. In addition, apertures 360 extend between outer and inner ends 350, 352. While end cap 10 is shown in FIGS. 13 and 14 with generally oval outer end 350, it is appreciated that end cap 310 may be shaped similarly to end cap 10 or in a variety of shapes to cooperate with a variety of spacers 12 and/or be formed without apertures 360. It is also appreciated that end caps 10 may vary in size to cooperate with a variety of spacers 12. Further, it is appreciated that end cap 310 could be formed to include, outer teeth 54, and/or an outer lip 56.

Another embodiment of the present invention is shown in FIGS. 15–17. End cap 410 includes an outer end 414, an inner end 416, and first and second side walls 420, 429 extending between outer and inner ends 414, 416. Second side wall 429 is a chamfer formed to facilitate inserting end cap 410 into spacer 12 and is tapered similarly to side wall 54 from first side wall portion 420 toward inner end 416.

Second side wall 429 is shown in FIG. 15. First and second side walls 420, 429 share inside surface 418 defining passageway 422. First side wall portion 420 also includes outside surface 421 while second side wall 429 includes outside surface 423. Six teeth 454 extend around the periphery of first side wall portion 420 and are coupled outside surface 421 in the same manner as teeth 78. Teeth 454 prevent end cap 410 from recessing too far within spacer 12. The engagement of first side wall portion 420 and teeth 454 with side wall 30 of spacer 12 provides the sole mechanical connection between end cap 410 and spacer 12. It is appreciated that the number of teeth 454 may be greater or fewer than six in accordance with the present disclosure. It is also appreciated that outer and inner ends 414, 416 may be positioned to lie generally parallel to one another or may be angled relative to one another.

As shown in FIGS. 15 and 16, end cap 410 also includes inside cross-sectional ends 424, 426 so that end cap 410 has a split-ring shape. Cross-sectional ends 424, 426 define a slot or cut-out portion 428. Slot 428 allows end cap 410 to be compressed in direction 430 as it is inserted into passageway 32 of spacer 12. End cap 410 is shown in its fully opened position in FIGS. 15 and 16 so that a lower outer diameter 432 (see FIG. 17) is greater than diameter 28 of passageway 32. As end cap 410 is compressed together in direction 430, it is sized for insertion within passageway 32 of spacer 12. Once inserted in spacer 12, end cap 410 expands toward its original shape and size thereby pressing against inner surface 40 of spacer 12 to insure a secure and tight fit.

FIG. 18 shows another alternate embodiment of the present invention. End cap 510 is identical to end cap 410 in nearly all respects and like reference numerals will be used to denote like components. End cap 510 includes teeth 554 coupled to outer surface 414 and extending away from side wall 420. Thus, outer end 414 is textured to provide further fixation for bone ingrowth.

Figure 19:
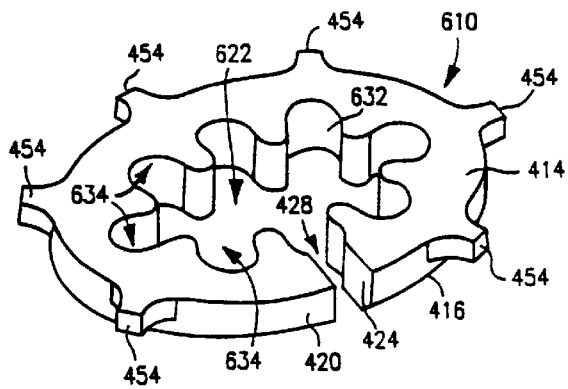
FIG. 19 is a perspective view of an end cap in accordance with an alternative embodiment of the present invention showing the end cap including a side wall having an outer surface and an irregularly shaped inner surface defining a passageway.
Figure 20:
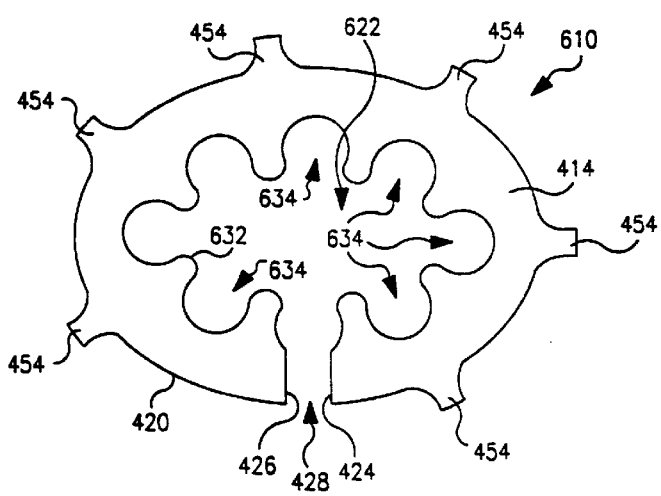
FIG. 20 is a top view of the end cap of FIG. 19 showing the inner surface of the side wall defining pockets that are spaced-apart from one another.
Figure 21:
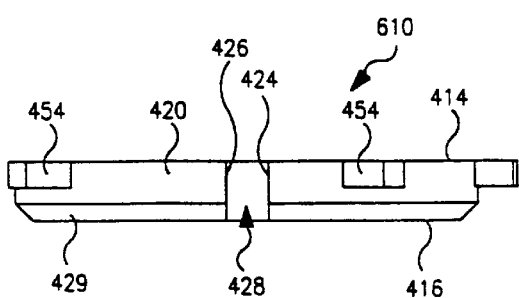
FIG. 21 is a front view of the end cap of FIG. 20 showing the slot extending between the outer and inner ends.
Figure 22:
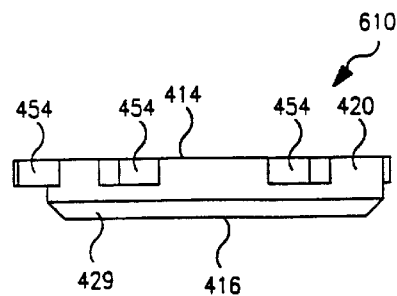
FIG. 22 is a side view of the end cap of FIG. 20 showing the side wall including a first side wall portion and a tapered second side wall portion.

As shown in FIGS. 19–22, end cap 610 is provided. End cap 610 is formed similarly to end cap 410 and like reference numerals will be used to denote like components. End cap 610 is formed to include a passageway 622 extending between outer and inner ends 414, 416. Passageway 622 is irregular in shape to maximize a surface area of an inner surface 632 of first and second side walls 420, 429. As shown in FIGS. 19 and 20, inner surface 632 defines pockets 634 spaced apart from one another. While end cap 610 having irregularly shaped passageway 622 with curved pockets 634 is illustrated and described, it is appreciated that end cap 610 may be formed to include a passageway having any number of shapes and sizes in accordance with the present disclosure.

Figure 23:
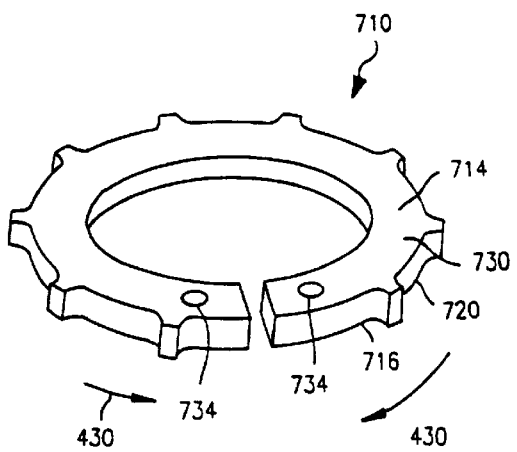
FIG. 23 is a perspective view of an end cap in accordance with an alternative embodiment of the present invention showing the end cap including a side wall formed without a chamfer.
Figure 24:
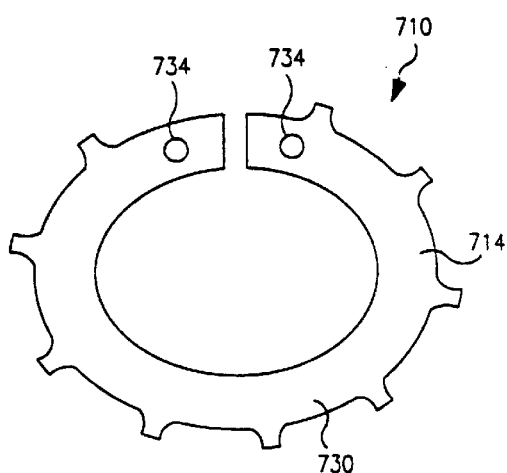
FIG. 24 is a top view of the end cap of FIG. 23 showing the outer end including apertures formed therein for receiving a compression instrument.
Figure 25:
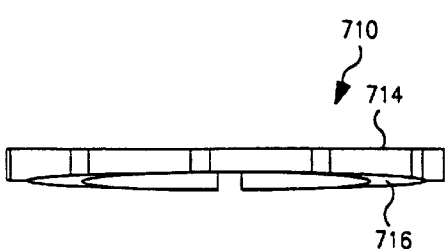
FIG. 25 is a back view of the end cap of FIG. 23 showing the outer and inner end positioned to lie at an angle relative to one another.
Figure 26:
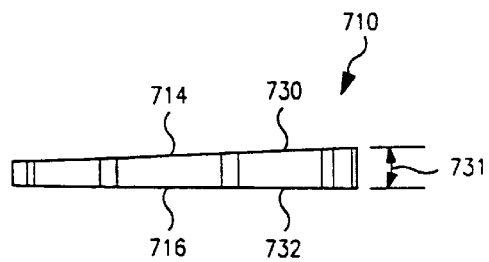
FIG. 26 is a side view of the end cap of FIG. 23 showing the outer and inner end positioned to lie at an angle relative to one another.

Referring now to FIGS. 23–26, end cap 710 is provided in accordance with the present invention. End cap 710 is formed similarly to end cap 410 and like reference numerals will be used to denote like components. End cap 710 includes a side wall 720 extending between inner and outer ends 714, 716. Side wall 720 is formed without a chamfer. In addition, as shown in FIGS. 25 and 26, inner and outer ends 714, 716 are positioned to lie at a predetermined angle 731 relative to one another and are formed to include different surfaces 730, 732, such as, for example porous surface 69 and serrated surface 70. As shown in FIGS. 23 and 24, end cap 710 includes apertures 734 that receive an instrument (not shown) used to compress end cap in direction 430 to be inserted into passageway 32 of spacer 12. Since side wall 720 is not tapered, the surgeon may insert either inner or outer end 714, 716 into passageway 32 so that the desired surface 69, 70 faces away from passageway 32 for engagement with vertebral body 48. It is appreciated that inner and outer ends may be positioned at a variety of angles relative to one another and may be positioned to lie in a generally parallel relationship as well in accordance with the present disclosure.

FIGS. 27–30 illustrate an end cap 810 in accordance with still another embodiment of the present invention. End cap 810 fits on outer surface 42 of spacer 12 instead of within passageway 32 as previously described end caps 10, 110, 210, 310, 410, 510, 610, and 710. End cap 810 includes an outer end 814, an inner end 816, and a crescent-shaped side wall 820 extending between outer and inner ends 814, 816. It is appreciated that end cap may be formed into circular, oval, or any complex polynomial shape in accordance with the present disclosure.

Crescent-shaped side wall 820 includes an inside surface 818 defining a passageway 822 and outside surface 821. A projection or lip 854 extends about the periphery of side wall 820 adjacent to outer end 814 into passageway 822. Lip 854 prevents end cap 810 from recessing too far within spacer 12. It is appreciated that the number of lips 854 may be greater than one in accordance with the present disclosure. It is also appreciated that outer and inner ends 814, 816 may be positioned to lie generally parallel to one another or may be angled relative to one another.

Figure 28:
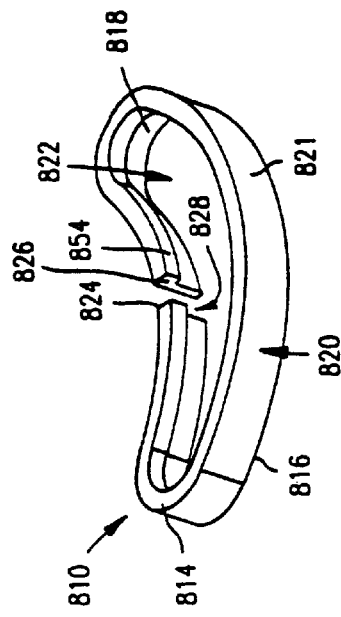
FIG. 28 is a top perspective view of the end cap of FIG. 27 showing the side wall including an inner surface defining a passageway and a lip extending from the side wall into the passageway.
Figure 30:
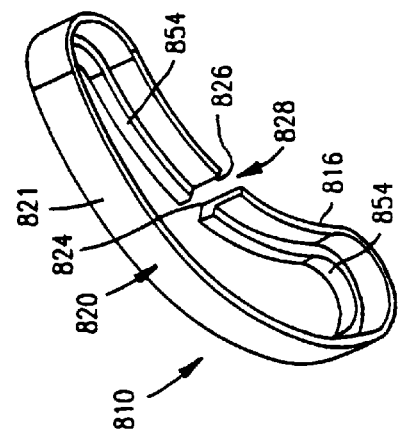
FIG. 30 is a bottom perspective view of the end cap of FIG. 27.
Figure 27:
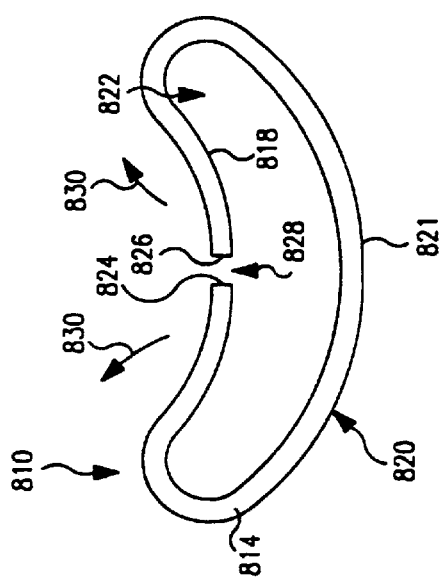
FIG. 27 is a top view of an end cap in accordance with an alternative embodiment of the present invention showing the end cap including a crescent-shaped side wall formed for expansion from its original shape to fit over the end of the spacer.
Figure 29:
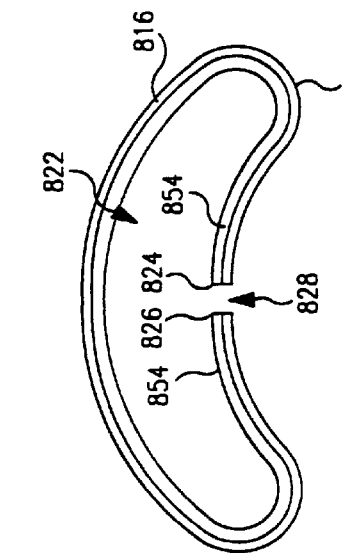
FIG. 29 is a bottom view of the end cap of FIG. 27 showing the lip extending into the passageway.

As shown in FIGS. 27 and 28, end cap 810 also includes inside cross-sectional ends 824, 826 defining a slot or cut-out portion 828. Slot 828 allows end cap 810 to expand in direction 830 such than inner surface 818 is sized to extend about outer surface 42 of side wall 30 of spacer 12. Once positioned about end 24 of spacer 12, end cap 810 compresses toward its original shape and size shown in FIG. 27, thereby pressing against outer surface 42 of spacer 12 to insure a secure and tight fit. Lip 854 contacts end 24 of spacer 12 to resist axial loads. In addition, lip provides the same support as teeth 78 provide such that end cap 810 cannot recess about side wall 30 of spacer 12 toward end 26. The engagement of side wall 820 and lip 854 with side wall 30 of spacer 12 provides the sole mechanical connection between end cap 810 and spacer 12.

Therefore, end caps 10, 11, 210, 310, 410, 510, 610, 710, and 810 are formed to cooperate with spacers to form spacer assemblies for use in spinal surgeries. End caps 10, 11, 210, 310, 410, 510, 610, 710, and 810 reinforce spacers that are used in spinal and trauma surgeries to increase stability and resistance to shear forces. End caps of the present invention fit within the spacer, on the outside of the spacer, or over the spacer and are coupled to the spacer by a taper or by split-ring forces. End caps 10, 11, 210, 310, 410, 510, 610, 710, and 810 are preferably self-locking in or on spacer 12. In addition, end caps of the present invention may be formed with a variety of different polynomial shapes to fit a variety of spacer shapes and have a variety of surface coatings or textures to promote bone growth or anti-skid features to prevent movement against bone increasing stability. At least one projection extends from the end cap toward the spacer to prohibit the end cap from slipping within a passageway of the spacer body.

Although the invention has been described in detail with reference to a preferred embodiment, variations and modifications exist within the scope and spirit of the invention as described and defined in the following claims.

What is claimed is:

1. A spacer assembly for use in spinal surgeries, the assembly comprising:

a spacer formed to include opposite ends and a side wall extending between the opposite ends, and at least one end cap coupled to at least one of the opposite ends, each of the at least one end caps including an inner end facing the spacer, an outer end, and a side wall extending between the inner and outer ends and engaging the side wall of the spacer to provide a mechanical connection between the at least one cap and the spacer, the side wall of the end cap including a slot extending between the outer and inner ends.

2. The spacer assembly of claim 1, wherein the spacer includes a passageway extending between the opposite ends and the inner end of the end cap extends into the passageway.

3. The spacer assembly of claim 2, wherein the side wall of the end cap converges from the outer end toward the inner end.

4. The spacer assembly of claim 3, wherein the end cap includes a projection coupled to the side wall of the end cap and formed for engagement with the spacer.

5. The spacer assembly of claim 3, wherein the outer end is formed to include a porous coating.

6. The spacer assembly of claim 3, wherein the outer end includes a serrated surface.

7. The spacer assembly of claim 2, wherein the end cap includes a projection that extends away from the side wall of the end cap into engagement with the spacer.

8. The spacer assembly of claim 2, wherein the end cap includes projections spaced-apart from one another and formed for engagement with the spacer.

9. The spacer assembly of claim 1, wherein the end cap includes projections spaced-apart from one another and formed for engagement with the spacer.

10. The spacer assembly of claim 1, wherein the side wall of the end cap includes an inner surface that defines a passageway between the inner and outer ends.

11. The spacer assembly of claim 10, wherein the inner surface of the side wall is generally cylindrical in shape.

12. The spacer assembly of claim 1, wherein the end cap is formed as a solid plate including apertures extending between the outer and inner surfaces.

13. The spacer assembly of claim 1, wherein at least one of the ends of the spacer includes peaks and valleys.

14. The spacer assembly of claim 13, wherein the end cap includes projections coupled to the side wall of the end cap and formed for extension between the peaks and engagement with the valleys of the spacer.

15. The spacer assembly of claim 13, wherein the end cap includes a projection coupled to the side wall of the end cap and formed for engagement with the peaks of the spacer.

16. A spacer assembly for use in spinal surgeries, the assembly comprising:

a spacer formed to include opposite ends and a side wall extending between the opposite ends, and at least one end cap coupled to at least one of the opposite ends, each of the at least one end caps including an inner end facing the spacer, an outer end, and a side wall extending between the inner and outer ends and engaging the side wall of the spacer to provide a mechanical connection between the at least one cap and the spacer and the side wall of the spacer includes an outer surface and the side wall of the end cap is coupled to the outer surface.

17. The spacer assembly of claim 16, wherein the side wall of the end cap includes a slot extending between the outer and inner ends.

18. The spacer assembly of claim 17, wherein the side wall of the end cap defines a passageway and the end cap further includes at least one projection extending into the passageway of the side wall and engaging the spacer.

19. A spacer assembly for use in spinal surgeries, the assembly comprising:

a spacer formed to include opposite ends and a side wall extending between the opposite ends, and end caps coupled to the opposite ends respectively, each of said end caps including an inner end facing the spacer, an outer end, a side wall extending between the inner and outer ends, and at least one projection extending from the side wall, the engagement of the end cap side wall with the side wall of the spacer and the at least one projection with the side wall with the respective opposite end of the spacer providing the sole mechanical connection between the spacer and the end caps, and the side wall of the end cap including a slot extending between the inner and outer ends.

20. The spacer assembly of claim 19, wherein the opposite ends are formed to include peaks and valleys.

21. The spacer assembly of claim 20, wherein the at least one projection engages at least one of the peaks of the respective opposite ends.

22. The spacer assembly of claim 20, wherein the at least one projection engages at least one of the valleys of the respective opposite ends.

23. The spacer assembly of claim 19, wherein the spacer includes a passageway extending between the opposite ends and the inner end of the end cap extends into the passageway.

24. The spacer assembly of claim 19, wherein the side wall of the spacer includes an outer surface and the side wall of the end cap is coupled to the outer surface.

25. The end cap of claim 19, wherein the outer end of the end cap is generally circular in shape.

26. The end cap of claim 19, wherein the outer end of the end cap includes a coating formed to promote bone growth.

27. The end cap of claim 19, wherein the side wall of the end cap includes a generally cylindrical inner surface defining a passageway.

28. A spacer assembly for use in spinal surgeries, the assembly comprising:

a spacer formed to include opposite ends and a side wall extending between the opposite ends, and end caps coupled to the opposite ends respectively, each of said end caps including an inner end facing the spacer, an outer end, a side wall extending between the inner and outer ends, and at least one projection extending from the side wall, the engagement of the end cap side wall with the side wall of the spacer and the at least one projection with the side wall with the respective opposite end of the spacer providing the sole mechanical connection between the spacer and the end caps, the spacer including a passageway extending between the opposite ends and the inner end of the end cap extends into the passageway, and the side wall of the end cap is tapered.

29. A spacer assembly for use in spinal surgeries, the assembly comprising:

a spacer formed to include opposite ends and a side wall extending between the opposite ends, and end caps coupled to the opposite ends respectively, each of said end caps including an inner end facing the spacer, an outer end, a side wall extending between the inner and outer ends, and at least one projection extending from the side wall, the engagement of the end cap side wall with the side wall of the spacer and the at least one projection with the side wall with the respective opposite end of the spacer providing the sole mechanical connection between the spacer and the end caps, the side wall of the spacer includes an outer surface and the side wall of the end cap is coupled to the outer surface and the side wall of the end cap includes a slot extending between the outer and inner ends.

30. An end cap formed for use with a spacer having opposite ends in a spinal surgery, the end cap comprising:

an inner end, an outer end, a side wall extending between the inner and outer ends, and at least one projection extending from the side wall, the side wall including a slot extending between the outer and inner ends and being adapted to provide a mechanical connection between the end cap and the spacer to couple the end cap and spacer together.

31. The end cap of claim 30, wherein the side wall includes an inner surface defining a passageway and an outer surface.

32. The end cap of claim 31, wherein the inner surface of the side wall is generally cylindrical in shape.

33. A spacer assembly for use in spinal surgeries, the assembly comprising:

a spacer formed to include opposite ends and a side wall extending between the opposite ends, and at least one end cap coupled to at least one of the opposite ends, each of the at least one end caps including an inner end facing the spacer, an outer end having a serrated surface, and a side wall extending between the inner and outer ends and engaging the side wall of the spacer to provide a mechanical connection between the at least one cap and the spacer, wherein the side wall of the end cap includes a slot extending between the outer and inner ends.

* * * * *

UNITED STATES PATENT AND TRADEMARK OFFICE
Certificate

Patent No. 6,086,613

Patented: July 11, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas S. Camino, Eldersburg, MD; John D. Malone, Cumberland, RI; Lutz Biedermann, Villingen, Germany; and Helmar Rapp, DeiBlingen, Germany.

Signed and Sealed this Twenty-ninth Day of April 2003.

KEVIN P. SHAVER
*Supervisory Patent Examiner*
Art Unit 3732